(12) United States Patent
Sohn et al.

(10) Patent No.: US 9,212,108 B2
(45) Date of Patent: *Dec. 15, 2015

(54) REMOVAL OF LIGHT ALKYLATED AROMATICS FROM THE HEAVY ALKYLATED AROMATICS STREAM

(71) Applicant: UOP LLC, Des Plaines, IL (US)

(72) Inventors: Stephen W. Sohn, Arlington Heights, IL (US); Mark G. Riley, Hinsdale, IL (US); Michael A. Moore, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 123 days.

This patent is subject to a terminal disclaimer.

(21) Appl. No.: 14/069,771

(22) Filed: Nov. 1, 2013

(65) Prior Publication Data

US 2015/0126770 A1    May 7, 2015

(51) Int. Cl.
| | |
|---|---|
| *C07C 6/06* | (2006.01) |
| *C07C 2/64* | (2006.01) |
| *C07C 303/20* | (2006.01) |
| *C07C 6/12* | (2006.01) |
| *C10G 29/20* | (2006.01) |
| *C10G 53/02* | (2006.01) |

(52) U.S. Cl.
CPC ... *C07C 6/06* (2013.01); *C07C 2/64* (2013.01); *C07C 6/126* (2013.01); *C07C 303/20* (2013.01); *C10G 29/205* (2013.01); *C10G 53/02* (2013.01); *C10G 2400/30* (2013.01)

(58) Field of Classification Search
None
See application file for complete search history.

(56) References Cited

U.S. PATENT DOCUMENTS

| | | | |
|---|---|---|---|
| 2,456,119 A | 12/1948 | Friedman | |
| 2,933,451 A | 4/1960 | Kooijman | |
| 3,206,519 A | 9/1965 | Eberhardt | |
| 3,422,161 A | 1/1969 | Lavigne | |
| 4,463,205 A | 7/1984 | Spinner | |
| 4,523,045 A * | 6/1985 | Vora | 585/254 |
| 4,774,377 A | 9/1988 | Barger | |
| 5,157,158 A | 10/1992 | Berna Tejero | |
| 6,069,285 A | 5/2000 | Fritsch | |
| 6,596,680 B2 | 7/2003 | Kott | |
| 6,995,127 B1 | 2/2006 | Smith | |
| 7,098,370 B2 | 8/2006 | Travers | |
| 7,638,666 B2 * | 12/2009 | Sohn et al. | 585/323 |
| 7,652,182 B2 * | 1/2010 | Sohn et al. | 585/323 |
| 7,692,055 B2 | 4/2010 | Sohn | |
| 7,781,632 B2 | 8/2010 | Glover | |
| 8,034,973 B2 | 10/2011 | Goncalvez De Almeida | |
| 8,293,698 B2 | 10/2012 | Le Coent | |
| 8,389,786 B2 | 3/2013 | Riley | |
| 8,431,759 B1 | 4/2013 | Sohn | |
| 2004/0164000 A1 * | 8/2004 | Abazajian | 208/143 |
| 2005/0019293 A1 | 1/2005 | Suriano | |
| 2011/0183852 A1 | 7/2011 | Yeung | |

OTHER PUBLICATIONS

PCT International Search Report for PCT/US2014/057713, mailing date Jan. 5, 2015.

* cited by examiner

*Primary Examiner* — Karl J Puttlitz

(57) ABSTRACT

A process for increasing the production of monoalkylbenzenes is presented. The process includes utilizing a transalkylation process to convert dialkylbenzenes to monoalkylbenzenes. The feed to the transalkylation process has alkylated toluenes and alkylated ethylbenzenes and other alkylated aromatics having small alkyl groups with less than 8 carbons removed to improve the efficiency of the transalkylation process. The recycled dialkylbenzenes and a portion of the recycled benzene are converted to monoalkylbenzenes.

13 Claims, 1 Drawing Sheet

US 9,212,108 B2

REMOVAL OF LIGHT ALKYLATED AROMATICS FROM THE HEAVY ALKYLATED AROMATICS STREAM

FIELD OF THE INVENTION

The present invention relates to the alkylation of benzene. In particular, the present invention relates to the conversion of dialkylbenzenes to monoalkylbenzenes.

BACKGROUND

The alkylation of benzene with olefins produces a variety of alkylbenzene compounds that have various commercial uses. Examples include the alkylation of benzene with olefins having 8 to 16 carbons for the production intermediate compounds in the manufacture of detergents. The alkylbenzenes are sometimes referred to as phenylalkanes, and are produced as a commodity in large scale facilities worldwide with production rates of between 50,000 and 200,000 metric tonnes per year. The alkylation process comprises reacting benzene with an olefin in the presence of a catalyst at elevated temperatures. The catalysts can be homogeneous or heterogeneous catalysts such as hydrogen fluoride, aluminum chloride, silica alumina, or zeolitic catalysts.

The desired alkylated compounds are monoalkylated aromatic compounds. Monoalkylated aromatic compounds include linear alkylbenzenes (LAB), which are used to form linear alkylbenzene sulfonates (LABS), a common compound used in the manufacture of detergents. Two common reactions for production of monoalkylated aromatic compounds are alkylation of aromatic compounds such as benzene and transalkylation of polyalkylated aromatic compounds. One aspect of benzene alkylation has been the use of high benzene to olefin ratios for the production of alkylbenzene production. The energy cost to recover the excess benzene has driven process designs to reduce the amount of benzene supplied to the reaction zone. This reduction has resulted in an increase in the amount of dialkylbenzene and trialkylbenzene byproducts produced in alkylation.

The desire to convert these polyalkylated benzene to monoalkylated benzene has resulted in further developments related to the transalkylation process. The transalkylation process reacts the polyalkylated aromatic compound with benzene to form a monoalkylated product, and thereby to increase yields of monoalkylated benzene. Both the alkylation and transalkylation processes involve the use of benzene in a relatively high molar ratio with respect the olefin or polyalkylated aromatic compound. The transalkylation process for producing a monoalkylated benzene product can be further complicated by the presence of polyalkylated benzenes that have alkyl groups having fewer carbon numbers than desired.

Currently, monoalkylated benzenes are desired, and polyalkylated benzenes are less desired by-products that need to be removed or need to be recycled to try and produce more monoalkylated benzenes. One method of reducing the amount of polyalkylated benzenes is to increase the benzene to olefin ratio used during alkylation. Another method of reducing polyalkylated benzenes is to pass the polyalkylbenzenes through a transalkylation reactor. However, the industry is striving to reduce the benzene to olefin ratio, and the usual method is to use many small beds with decreasing ratios as the benzene and olefins pass through successive beds. The cost of producing a pure benzene stream is expensive, and the cost of separating and recycling benzene is energy intensive and therefore expensive.

Methods of improving the recovery and usage of benzene, which also optimize the processing of alkylated benzenes that have alkyl groups having fewer carbon numbers than desired, can result in substantial savings in energy and expense.

SUMMARY

The present process provides a method for producing high quality alkylbenzenes without the need to separate aromatics from the hydrocarbon feedstream comprising olefins that are used in the alkylation of benzene. The process includes passing a hydrocarbon stream comprising olefins, paraffins and aromatics in the C9 to C14 range to an alkylation zone. A benzene stream is passed to the alkylation zone and reacted with the hydrocarbon stream to generate a process stream comprising benzene, monoalkylbenzenes and heavy alkylbenzenes. The process stream is separated in a first separation unit to generate a first stream comprising benzene for recycle to the alkylation unit, a second stream comprising monoalkylated benzenes having carbon numbers between C15 and C20, and a third stream comprising heavy alkylbenzenes. The second stream is an intermediate product stream for downstream production of sulfonated alkylbenzenes.

The third stream is passed to a second separation unit to generate a first separation stream comprising light alkylated aromatics and a second separation stream comprising dialkylbenzenes. In the context of the present invention, dialkylbenzenes refers to benzene that has been alkylated with two olefins from the C9 to C14 feedstream. This is to differentiate the dialkylbenzenes from alkylated aromatics that include alkylated toluene, alkylated ethylbenzene, and other alkylated aromatics having small alkyl groups with less than 8 carbons. The second separation stream is passed to a transalkylation zone, along with a benzene stream to generate a transalkylation zone effluent stream. The transalkylation effluent stream comprises monoalkylated benzenes and is passed to the first separation unit to recover the monoalkylated benzenes.

Other objects, advantages and applications of the present invention will become apparent to those skilled in the art from the following detailed description and drawings.

DETAILED DESCRIPTION

Figure 1:
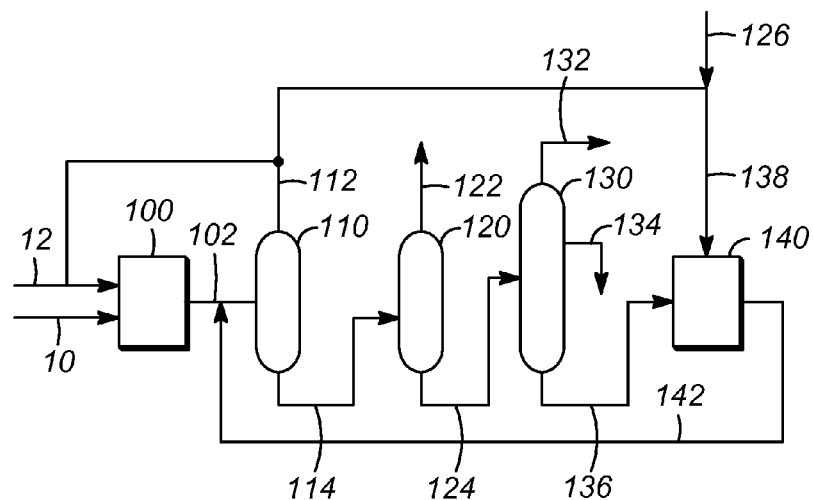
FIG. 1 shows the process for generating monoalkylbenzenes, including increasing the yields through transalkylation of heavy alkylbenzenes.

The process of manufacturing linear alkyl benzenes (LABs) for use in detergents includes many steps. The process of generating LABs includes reacting a linear alkyl group, typically comprising a C9 to C14 alkyl group, with benzene to generate the LAB. The production of LABs also generates heavy alkylated benzenes (HABs), which are polyalkylated benzene compounds. As used hereinafter, heavy alkylbenzenes refer to polyalkylated benzenes that have been alkylated from two or more olefins from the olefin feedstream. These include dialkylbenzenes and trialkylbenzenes. The heavy alkylbenzenes can be sent to a trans-alkylation unit with benzene to convert the polyalkylated benzenes to monoalkylated benzenes, thereby increasing yields. Transalkylation is shown to increase yields, as seen in U.S. Pat. Nos. 8,350,110; 7,692,055; 7,576,247; 7,652,182; 7,642,389;

and 7,638,666, which are incorporated by reference. The process also generates other alkylated aromatics, such as alkylated toluene. Although alkylated toluene is considered a dialkylbenzene, for purposes of the present disclosure, dialkylbenzene refers to benzene that has been alkylated with two olefins, each having 9 to 14 carbon atoms. Other alkylated aromatics, such as alkylated toluene will be referred to as light alkylated aromatics.

The alkylation of benzene involves the processing of the precursors, and the intermediate product streams to remove, or convert, undesirable compounds, such as aromatics generated in the process of dehydrogenating paraffins, to prevent the generation of thousands of tons of essentially waste material. It has been found that the aromatic by-products formed from the dehydrogenation process are detrimental to the alkylation processes. One aspect in the commercial production of LABs is the purification of the olefins in upstream processes which can worsen the economics of detergent production in some circumstances. Processes for removing aromatic by-products can be found in U.S. Pat. Nos. 5,245,094; 5,276,231; and 5,334,793, which are incorporated herein by reference. The production of the olefins stream used in the alkylation process is generally formed from the separation of a hydrocarbon stream comprising hydrocarbons in a desired range, and then processing the stream to generate a stream enriched in olefins. As an example, a hydrocarbon stream comprising C9 to C14 hydrocarbons is separated from a larger hydrocarbon pool. The stream of C9 to C14 hydrocarbons is further separated to generate a paraffin stream comprising, primarily normal paraffins in the C9 to C14 range. The normal paraffins are then dehydrogenated to generate an olefin stream. The normal paraffins generated and passed to the dehydrogenation unit preferably have a linearity of greater than 85% normal paraffins. The dehydrogenation process also generates diolefins, acetylenes and aromatics in the C9 to C14 range. Selective hydrogenation can treat and remove a portion of the diolefins and acetylenes, however there are aromatic compounds that remain and present downstream problems for producing a quality linear alkylbenzene product. Aromatics in the process stream can be removed, but the economics of detergent production can be improved for some detergent producers by not removing the aromatics or undesired by-products upstream of the alkylation process.

The heavy alkylated benzenes formed in the alkylation unit include not only dialkylbenzene, but also other alkylated aromatics such as alkylated aromatics generated by the dehydrogenation process. When the stream containing the HABs is passed to the transalkylation unit to convert the HABs to LABs, the transalkylation process efficiency is lowered due to the presence of other alkylated aromatics and lead to waste and increased burdens on downstream fractionation.

The process seeks to alkylate benzene with C9 to C14 olefins, and preferably to use C10 to C13 olefins, with small amounts of C9 and/or C14 olefins. Hereinafter, the term C10 to C13 is intended to allow for the inclusion of small amounts of C9 and/or C14 compounds. The feedstream comprising C10 to C13 olefins is generated by a dehydrogenation process that dehydrogenates paraffins in the C10 to C13 range. The dehydrogenation process generates a feedstream that includes paraffins, or unreacted material; olefins; and other dehydrogenated compounds that include aromatics. These are aromatics in the C10 to C13 range and include butylbenzene, and aromatics up to heptylbenzene. More commonly, aromatics such as methyl butyl benzene are generated. These aromatics present problems in the product purity downstream. After alkylation of benzene with the feedstream, the process stream will comprise unreacted feed having hydrocarbons in the C10 to C13 range, including lighter aromatics; monoalkylated benzene having carbon numbers in the 16 to 19 range; light alkylated aromatics having carbon numbers in the 18 to 24 range, and dialkylbenzenes having carbon numbers in the 26 to 32 range. The dialkylated aromatics can be represented by n,n'-dialkylbenzene, wherein n represents the carbon number of one of the alkyl groups and n' represents the carbon number for the second alkyl group. In the case of dialkylbenzenes that are desired for passage to the transalkylation unit, both n and n' have a value between 10 and 14, inclusive. The light alkylated aromatics, which are also dialkylbenzenes, have n between 1 and 9 and n' between 10 and 14, inclusive.

The efficiency of the transalkylation process to produce mono-alkylbenzenes in the C10 to C14 range is adversely affected by the light alkylated aromatics. The current state of the art is to remove aromatics upstream of the alkylation process, which can entail a more costly step for the removal of these aromatics. The present process removes that step, and instead separates the alkylated aromatics that have smaller alkyl groups on the molecules before passing the heavy alkylates to the transalkylation reaction unit. The passage of the light alkylbenzene can result is a product stream having monoalkylated benzene where the alkyl groups have less than 9 carbons, and subsequently the product stream is of poor quality. Therefore, the removal of the light alkylbenzene from the transalkylation feed improves the product quality.

The process for the production of monoalkylbenzenes, as shown in FIG. 1, includes passing a hydrocarbon stream 10 and a benzene stream 12 to an alkylation zone 100. The hydrocarbon stream includes olefins, paraffins and aromatics in the C10 to C13 range. The alkylation zone 100 generates a process stream 102 comprising benzene, and alkylbenzenes. The process stream 102 is past to a first separation unit 110 to generate a first stream 112 comprising benzene, and a second stream 114 comprising monoalkylbenzenes, paraffins and heavier alkylbenzenes. The second stream 114 is passed to a second separation unit 120 to separate paraffins and non-aromatics from the alkylbenzenes and generate a third stream 122 comprising paraffins and a fourth stream 124 comprising alkylbenzenes. The fourth stream 124 is passed to a third separation unit 130 to generate a monoalkylbenzene product stream 132, an intermediate stream 134 comprising light alkylbenzenes, and a heavy alkylbenzene stream 136. The third separation unit 130 can comprise a divided wall column, or can comprise two distillation columns for separation of the fourth stream 124 into three separate streams. Other separation designs can also be contemplated to provide the desired separation. The monoalkylated benzene stream 132 is passed downstream for processing into a detergent. The monoalkylated benzene stream is passed to a sulfonation unit to generate a monoalkylbenzene sulfonate. The separation units will generally comprise distillation or fractionation columns, but it is not intended to limit the separation units to these devices.

The heavy alkylbenzene stream 136 is passed to a transalkylation zone 140 along with a benzene stream 138 to generate a transalkylation effluent stream 142 comprising monoalkylbenzenes. The transalkylation effluent stream 142 is passed to the first separation unit 110 to recover the monoalkylbenzenes.

In one embodiment, the hydrocarbon stream is generated by converting paraffins to olefins through passing a paraffin stream through a dehydrogenation system to generate a dehydrogenated stream comprising olefins and other unsaturated hydrocarbons. The dehydrogenated stream can be passed through a selective hydrogenation unit to selectively hydrogenate diolefins and acetylenes.

The aromatics stream 12 is preferably comprised of benzene. However, toluene and ethylbenzene can be used when the alkylbenzene does not require passing a fraction to a transalkylation unit.

The first stream 112 comprising benzene, or a portion thereof, can be recycled to the alkylation zone 100. A portion of the first stream 112 can also be passed to the transalkylation zone 140. Fresh benzene 126 can also be introduced into the process to make up for benzene consumed in the alkylation and transalkylation reactions. The makeup benzene 126 and a portion of the recycle benzene 112 can be combined for form the benzene feedstream 138 to the transalkylation unit 140.

In one embodiment, a portion of the transalkylation effluent 142 is passed to the transalkylation unit 140.

Figure 2:
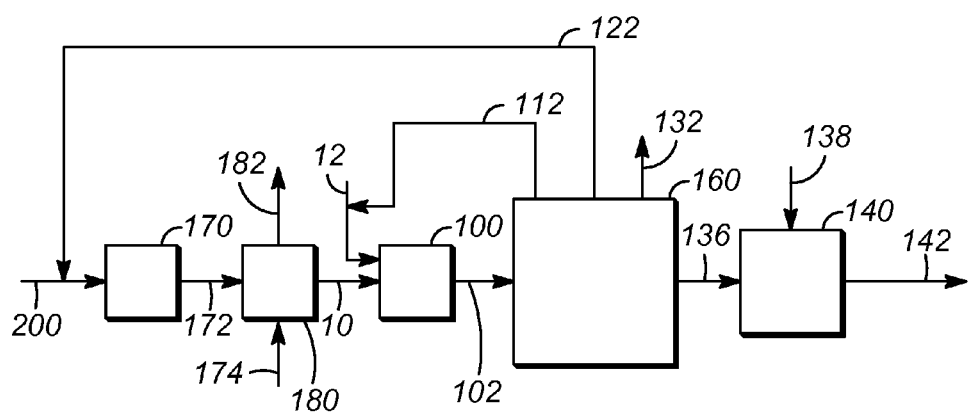
FIG. 2 shows the process including the generation of linear olefins with the recycling of paraffins and benzene.

In one embodiment, the process is further integrated with a paraffin dehydrogenation process. The process, as shown in FIG. 2, includes an olefin feedstream 10 and a benzene feedstream 12 passed to the alkylation unit 100. The alkylation unit 100 generates an alkylbenzene process stream 102 and is passed to a separation unit 160. The separation unit 160 comprises multiple fractionation columns as described above for FIG. 1, and generates multiple streams, including a benzene stream 112, a paraffin stream 122 and a heavy alkylbenzene stream 136. The olefin feedstream 10 is generated from an initial paraffin stream 200. The initial paraffin stream 200, can be combined with the paraffin stream 122 from the separation unit 160. The combined streams are passed to a dehydrogenation unit 170 to generate a process stream 172 comprising olefins, diolefins, acetylenes, aromatics, and unreacted paraffins. Unreacted paraffins are passed through, and recycled when separated from the effluent stream of the alkylation unit 100. The process stream 172 is passed to a selective hydrogenation unit 180 with a hydrogen stream 174 to convert the diolefins and acetylenes to olefins to generate the feedstream 10 to the alkylation unit 100. The selective hydrogenation unit 180 can also include a fractionation unit for removing light compounds and hydrogen in a separate stream 182, before passing the feedstream 10 to the alkylation unit 100.

In one embodiment, the process can further include passing the monoalkylated benzene to a sulfonation unit to convert the monoalkylated benzene to monoalkylated benzene sulfonate.

Within the context of the present invention, the process uses a hydrocarbon stream comprising many hydrocarbons. This hydrocarbon stream is operated and selected to comprise primarily hydrocarbons in the C10 to C13 range. This includes paraffins, olefins and aromatic compounds. The desired monoalkylated benzenes generated in the alkylation unit will have a carbon number in the range from C15 to C20, which is generated from a C10 to C13 olefin alkylating a benzene compound. Light alkylated aromatics generated in the alkylation unit include alkylated toluene and alkylated ethylbenzene among other compounds, that can be formed in the alkylation unit. The light alkylated aromatics generated will have a carbon number in the range from C20 to C26, and generally from C18 to C28. Dialkylbenzenes generated in the alkylation unit will have carbon numbers in the range C26 to C32, and generally from C24 to C34, with trialkylbenzenes having higher carbon numbers.

The light alkylated aromatics need to be removed before passing the stream to a transalkylation unit to limit the amount of waste product that will be unusable for a commercial detergent product.

In one embodiment, the process for the production of monoalkylbenzene having 16 to 19 carbons includes passing a hydrocarbon feedstream comprising C10 to C13 hydrocarbons and an aromatics stream comprising benzene to an alkylation zone. The alkylation zone generates a process stream that includes monoalkylbenzenes, benzene and heavy alkylbenzenes. The heavy alkylbenzenes include dialkylbenzenes but also includes other alkylated aromatics that are lighter than dialkylbenzene. These light alkylated aromatics are a result of alkylation of aromatics generated by the dehydrogenation process in the hydrocarbon feedstream. These aromatics have smaller alkyl groups, having 7 or fewer carbons in the alkyl groups. Examples include methyl propylbenzene, butyl benzene, methyl hexylbenzene, heptylbenzene and many other aromatic products with one or more C1 to C7 alkyl groups affixed to the benzene prior to passing to the alkylation unit.

The process stream leaving the alkylation unit is passed to a first separation unit to generate a second stream comprising benzene and a third stream comprising monoalkylated benzenes, heavy alkylbenzenes, and other hydrocarbons. The third stream is passed to a second separation unit to generate an overhead stream comprising paraffins and a bottoms stream comprising alkylaromatics. The bottoms stream is passed to a third separation unit to generate the monoalkylated benzene product stream and a fourth stream comprising alkylated benzenes that are heavier than monoalkylated benzene. The product can be passed to a sulfonation unit to generate a sulfonated alkylbenzene.

The fourth stream is passed to a fourth separation unit to generate a fifth stream comprising dialkylbenzenes and heavier components having more than 26 carbons, such as trialkylbenzenes. The fourth separation unit also generates a sixth stream comprising the light alkylaromatics having from 20 to 26 carbons. The sixth stream can be passed to another downstream process unit for further processing.

The fifth stream is passed to a transalkylation zone, along with passing of a benzene stream to the transalkylation zone to generate a transalkylation effluent stream comprising monoalkylbenzenes. The transalkylation effluent stream is passed to the first separation unit to recover the monoalkylbenzenes. In one option, a portion of the transalkylation effluent stream can be passed back to the transalkylation zone.

In one embodiment, the hydrocarbon feedstream comprising C10 to C13 hydrocarbons is generated from a paraffin stream. The paraffins stream is passed to a dehydrogenation unit to generate a dehydrogenated stream comprising olefins, paraffins, aromatics and some diolefins and acetylenes. Optionally, the dehydrogenated stream can be passed to a selective hydrogenation unit to selectively hydrogenation acetylenes and diolefins, along with some hydrogenation of aromatics.

A portion of the benzene recovered in the first separation unit can be passed to the alkylation unit, and a second portion of the benzene from the first separation unit can be passed to the transalkylation unit.

This process relieves the need to remove aromatics from the hydrocarbon feedstream to the alkylation reactor, and allows for allows for some light aromatics to be alkylated and recovered for use in detergent manufacture, while maintaining the efficiency of the transalkylation unit in the generation of a transalkylation effluent stream comprising monoalkylated benzenes.

Specific Embodiments

While the following is described in conjunction with specific embodiments, it will be understood that this description is intended to illustrate and not limit the scope of the preceding description and the appended claims.

A first embodiment of the invention is a process for the production of monoalkylbenzenes, comprising: passing a hydrocarbon stream, comprising olefins, paraffins and aromatics in the C9 to C14 range, to an alkylation zone; passing an aromatics stream comprising benzene to the alkylation zone, wherein the alkylation zone is operated at alkylation conditions, to generate a process stream comprising paraffins, benzene, monoalkylbenzenes and heavy alkylbenzenes; separating the process stream, in a first separation unit, into a first stream comprising benzene, and a second stream comprising alkylbenzenes and paraffins; passing the second stream to a second separation unit to generate a third stream comprising paraffins, and a fourth stream comprising alkylbenzenes; passing the fourth stream to a third separation unit to generate a fifth stream comprising monoalkylated benzene, a sixth stream comprising light alkylated aromatics, and a seventh stream comprising dialkylbenzene; passing the seventh stream to a transalkylation zone; passing a benzene stream to the transalkylation zone, operated at transalkylation conditions to generate a transalkylation effluent stream comprising monoalkylbenzenes; and passing the transalkylation effluent stream to the first separation unit. An embodiment of the present invention includes the prior embodiment in this paragraph wherein the hydrocarbon stream comprising olefins is generated by a paraffins-to-olefins dehydrogenation process, and wherein the process further comprises: passing a paraffin stream to a dehydrogenation system to generate a dehydrogenated stream; and passing the dehydrogenated stream to a selective hydrogenation unit to generate the hydrocarbon stream comprising olefins. An embodiment of the invention is one, any or all of prior embodiments in this paragraph up through the first embodiment in this paragraph further comprising passing the fifth stream to a sulfonation unit to convert monoalkylated benzene to monoalkylated benzene sulfonate. An embodiment of the invention is one, any or all of prior embodiments in this paragraph up through the first embodiment in this paragraph wherein the third stream comprising paraffins is passed to the paraffins-to-olefins dehydrogenation process. An embodiment of the invention is one, any or all of prior embodiments in this paragraph up through the first embodiment in this paragraph wherein a portion of the first stream comprising benzene is passed to the alkylation zone. An embodiment of the invention is one, any or all of prior embodiments in this paragraph up through the first embodiment in this paragraph wherein a portion of the first stream comprising benzene is passed to the transalkylation zone. An embodiment of the invention is one, any or all of prior embodiments in this paragraph up through the first embodiment in this paragraph further comprising passing a portion of the transalkylation effluent stream to the transalkylation zone.

A second embodiment of the invention is a process for the production of monoalkylbenzenes, comprising: passing hydrocarbon stream comprising C10 to C13 hydrocarbons and an aromatics stream to an alkylation zone to generate an alkylation process stream comprising paraffins, benzene, monoalkylbenzenes, and heavy alkylbenzenes; passing the alkylation process stream to a first separation unit to generate a first stream comprising benzene, and a second stream comprising paraffins and alkylbenzenes; passing the second stream to a second separation unit to generate a third stream comprising paraffins, and a fourth stream comprising alkylbenzenes; passing the fourth stream to a third separation unit to generate a fifth stream comprising monoalkylated benzenes having 16 to 19 carbons, a sixth stream comprising light alkylated aromatics having 20 to 26 carbons, and a seventh stream comprising dialkylbenzenes having 26 or more carbons; passing the seventh stream to a transalkylation zone; passing a benzene stream to the transalkylation zone, operated at transalkylation conditions to generate a transalkylation effluent stream comprising monoalkylbenzenes; and passing the transalkylation effluent stream to the first separation unit. An embodiment of the invention is one, any or all of prior embodiments in this paragraph up through the second embodiment wherein the hydrocarbon stream comprising C10 to C13 hydrocarbons is generated by a paraffins-to-olefins dehydrogenation process, and wherein the process further comprises: passing a paraffin stream without aromatics to a dehydrogenation system to generate a dehydrogenated stream; and passing the dehydrogenated stream to a selective hydrogenation unit to generate the hydrocarbon stream comprising C10 to C14 hydrocarbons. An embodiment of the invention is one, any or all of prior embodiments in this paragraph up through the second embodiment further comprising passing the second stream to a sulfonation unit to convert monoalkylated benzene to monoalkylated benzene sulfonate. An embodiment of the invention is one, any or all of prior embodiments in this paragraph up through the second embodiment wherein a portion of the first stream comprising benzene is passed to the alkylation zone. An embodiment of the invention is one, any or all of prior embodiments in this paragraph up through the second embodiment wherein a portion of the first stream comprising benzene is passed to the transalkylation zone. An embodiment of the invention is one, any or all of prior embodiments in this paragraph up through the second embodiment further comprising passing a portion of the transalkylation effluent stream to the transalkylation zone.

A third embodiment of the invention is a process for the production of linear alkylbenzenes, comprising: passing an alkylation effluent stream to a first separation zone to generate a first stream comprising benzene, a second stream comprising linear monoalkylbenzenes, a third stream comprising heavy alkylbenzenes and light alkylated aromatics, and a fourth stream comprising paraffins; passing the third stream to a second separation zone to generate a fifth stream comprising heavy alkylbenzenes and a sixth stream comprising light alkylated aromatics; and continuously supplying benzene and a portion of the fifth stream to a transalkylation zone, operated at transalkylation conditions to generate a transalkylation effluent stream. An embodiment of the invention is one, any or all of prior embodiments in this paragraph up through the third embodiment further comprising: continuously supplying benzene and a mixture of linear olefins to an alkylation zone, operated at alkylation conditions to generate the alkylation effluent stream comprising benzene, linear alkylbenzenes, and heavy alkylbenzenes, before passing the alkylation effluent stream to the first separation zone. An embodiment of the invention is one, any or all of prior embodiments in this paragraph up through the third embodiment wherein the mixture of linear olefins supplied to the alkylation zone comprise C10 to C13 olefins is generated by a paraffins-to-olefins dehydrogenation process, and wherein the process further comprises: passing a paraffin stream to a dehydrogenation system to generate a dehydrogenated stream; and passing the dehydrogenated stream to a selective hydrogenation unit to generate the mixture of linear olefins. An embodiment of the invention is one, any or all of prior embodiments in this paragraph up through the third embodiment further comprising passing the second stream to a sulfonation unit to convert monoalkylated benzene to monoalkylated benzene sulfonate. An embodiment of the invention is one, any or all of prior embodiments in this paragraph up through the third embodiment wherein the mixture of linear olefins comprise olefins in the C10 to C13 range. An embodiment of the invention is one, any or all of prior embodiments in this paragraph up through the third embodiment wherein the light alkylated aromatics are lighter than dialkylbenzenes. An embodiment of the invention is one, any or all of prior embodiments in this paragraph up through the third embodiment wherein the light alkylated aromatics comprise alkylated aromatics in the C20 to C26 carbon range.

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A process for the production of monoalkylbenzenes, comprising:
    passing a hydrocarbon stream, comprising olefins, paraffins and aromatics in the C9 to C14 range, to an alkylation zone;
    passing an aromatics stream comprising benzene to the alkylation zone, wherein the alkylation zone is operated at alkylation conditions, to generate a process stream comprising paraffins, benzene, monoalkylbenzenes and heavy alkylbenzenes;
    separating the process stream, in a first separation unit, into a first stream comprising benzene, and a second stream comprising alkylbenzenes and paraffins;
    passing the second stream to a second separation unit to generate a third stream comprising paraffins, and a fourth stream comprising alkylbenzenes;
    passing the fourth stream to a third separation unit to generate a fifth stream comprising monoalkylated benzene, a sixth stream comprising light alkylated aromatics, and a seventh stream comprising dialkylbenzene, wherein light alkylated aromatics comprise dialkylated aromatics with one alkyl group having less than 9 carbon atoms;
    passing the seventh stream to a transalkylation zone;
    passing a benzene stream to the transalkylation zone, operated at transalkylation conditions to generate a transalkylation effluent stream comprising monoalkylbenzenes; and
    passing the transalkylation effluent stream to the first separation unit.

2. The process of claim 1 wherein the hydrocarbon stream comprising olefins is generated by a paraffins-to-olefins dehydrogenation process, and wherein the process further comprises:
    passing a paraffin stream to a dehydrogenation system to generate a dehydrogenated stream; and
    passing the dehydrogenated stream to a selective hydrogenation unit to generate the hydrocarbon stream comprising olefins.

3. The process of claim 1 further comprising passing the fifth stream to a sulfonation unit to convert monoalkylated benzene to monoalkylated benzene sulfonate.

4. The process of claim 2 wherein the third stream comprising paraffins is passed to the paraffins-to-olefins dehydrogenation process.

5. The process of claim 1 wherein a portion of the first stream comprising benzene is passed to the alkylation zone.

6. The process of claim 1 wherein a portion of the first stream comprising benzene is passed to the transalkylation zone.

7. The process of claim 1 further comprising passing a portion of the transalkylation effluent stream to the transalkylation zone.

8. A process for the production of monoalkylbenzenes, comprising:
    passing hydrocarbon stream comprising C10 to C13 hydrocarbons and an aromatics stream to an alkylation zone to generate an alkylation process stream comprising paraffins, benzene, monoalkylbenzenes, and heavy alkylbenzenes;
    passing the alkylation process stream to a first separation unit to generate a first stream comprising benzene, and a second stream comprising paraffins and alkylbenzenes;
    passing the second stream to a second separation unit to generate a third stream comprising paraffins, and a fourth stream comprising alkylbenzenes;
    passing the fourth stream to a third separation unit to generate a fifth stream comprising monoalkylated benzenes having 16 to 19 carbons, a sixth stream comprising light alkylated aromatics having 20 to 26 carbons, and a seventh stream comprising dialkylbenzenes having 26 or more carbons, wherein light alkylated aromatics comprise dialkylated aromatics with one alkyl group having less than 9 carbon atoms;
    passing the seventh stream to a transalkylation zone;
    passing a benzene stream to the transalkylation zone, operated at transalkylation conditions to generate a transalkylation effluent stream comprising monoalkylbenzenes; and
    passing the transalkylation effluent stream to the first separation unit.

9. The process of claim 8 wherein the hydrocarbon stream comprising C10 to C13 hydrocarbons is generated by a paraffins-to-olefins dehydrogenation process, and wherein the process further comprises:
    passing a paraffin stream without aromatics to a dehydrogenation system to generate a dehydrogenated stream; and
    passing the dehydrogenated stream to a selective hydrogenation unit to generate the hydrocarbon stream comprising C10 to C14 hydrocarbons.

10. The process of claim 8 further comprising passing the second stream to a sulfonation unit to convert monoalkylated benzene to monoalkylated benzene sulfonate.

11. The process of claim 8 wherein a portion of the first stream comprising benzene is passed to the alkylation zone.

12. The process of claim 8 wherein a portion of the first stream comprising benzene is passed to the transalkylation zone.

13. The process of claim 8 further comprising passing a portion of the transalkylation effluent stream to the transalkylation zone.

* * * * *